United States Patent
Kim et al.

(10) Patent No.: US 11,654,195 B2
(45) Date of Patent: May 23, 2023

(54) ECO-FRIENDLY SMART PHOTOSENSITIZER AND PHOTO-STEM CELL THERAPY PRODUCT COMPRISING SAME

(71) Applicants: Jin Wang Kim, Seoul (KR); Jung Ok Lee, Seoul (KR); Hyun Ji Kim, Seoul (KR); Hyun Woo Kim, Seoul (KR)

(72) Inventors: Jin Wang Kim, Seoul (KR); Jung Ok Lee, Seoul (KR); Hyun Ji Kim, Seoul (KR); Hyun Woo Kim, Seoul (KR)

( * ) Notice: Subject to any disclaimer, the term of this patent is extended or adjusted under 35 U.S.C. 154(b) by 0 days.

(21) Appl. No.: 17/786,980

(22) PCT Filed: Nov. 26, 2020

(86) PCT No.: PCT/KR2020/017009
§ 371 (c)(1),
(2) Date: Jun. 17, 2022

(87) PCT Pub. No.: WO2021/125611
PCT Pub. Date: Jun. 24, 2021

(65) Prior Publication Data
US 2023/0088872 A1    Mar. 23, 2023

(30) Foreign Application Priority Data

Dec. 19, 2019   (KR) .................. 10-2019-0171174
Aug. 12, 2020   (KR) .................. 10-2020-0101343

(51) Int. Cl.
| | | |
|---|---|---|
| *A61K 47/00* | (2006.01) | |
| *A61P 35/00* | (2006.01) | |
| *A61K 41/00* | (2020.01) | |
| *A61K 47/69* | (2017.01) | |
| *A61K 47/61* | (2017.01) | |

(52) U.S. Cl.
CPC .......... *A61K 41/0057* (2013.01); *A61K 47/61* (2017.08); *A61K 47/6939* (2017.08); *A61P 35/00* (2018.01)

(58) Field of Classification Search
CPC .......... A61K 41/00; A61K 47/00; A61P 35/00
See application file for complete search history.

(56) References Cited

U.S. PATENT DOCUMENTS

| 5,438,071 A | 8/1995 | Clauss et al. |
| 2010/0222538 A1* | 9/2010 | Kwon ................... A61K 47/61 |
| | | 527/312 |

FOREIGN PATENT DOCUMENTS

| KR | 10-2011-0101338 A | 9/2011 |
| KR | 10-1791399 B1 | 10/2017 |
| KR | 10-2019-0133475 A | 12/2019 |
| KR | 10-2182630 B1 | 11/2020 |

OTHER PUBLICATIONS

Gabriel Kigen et al., "Enhancement of saquinavir absorption and accumulation through the formation of solid drug nanoparticles", Kigen and Edwards BMC Pharmacology and Toxicology, 2018, pp. 1-10, vol. 19, No. 79.
Binrui Cao et al., "Stem Cells Loaded with Nanoparticles as a Drug Carrier for In Vivo Breast Cancer Therapy", Adv Mater., Jul. 16, 2014, pp. 4627-4631, vol. 26, No. 27.
Korean Grant of Patent for KR 10-2020-0101343, dated Nov. 17, 2020.
International Search Report for PCT/KR2020/017009, dated Mar. 12, 2021.

* cited by examiner

*Primary Examiner* — Michael G. Hartley
*Assistant Examiner* — Jagadishwar R Samala
(74) *Attorney, Agent, or Firm* — Sughrue Mion, PLLC

(57) ABSTRACT

The present invention provides an eco-friendly smart photosensitizer comprising a conjugate of hydroxypropyl methylcellulose and porfimer sodium photosensitizer, and a photo-stem cell therapy product comprising the photosensitizer. The photosensitizer of the present invention can be advantageously used in various fields including anticancer therapy, stem cell therapy, and the like, without side effects.

7 Claims, 18 Drawing Sheets

[FIG.1]
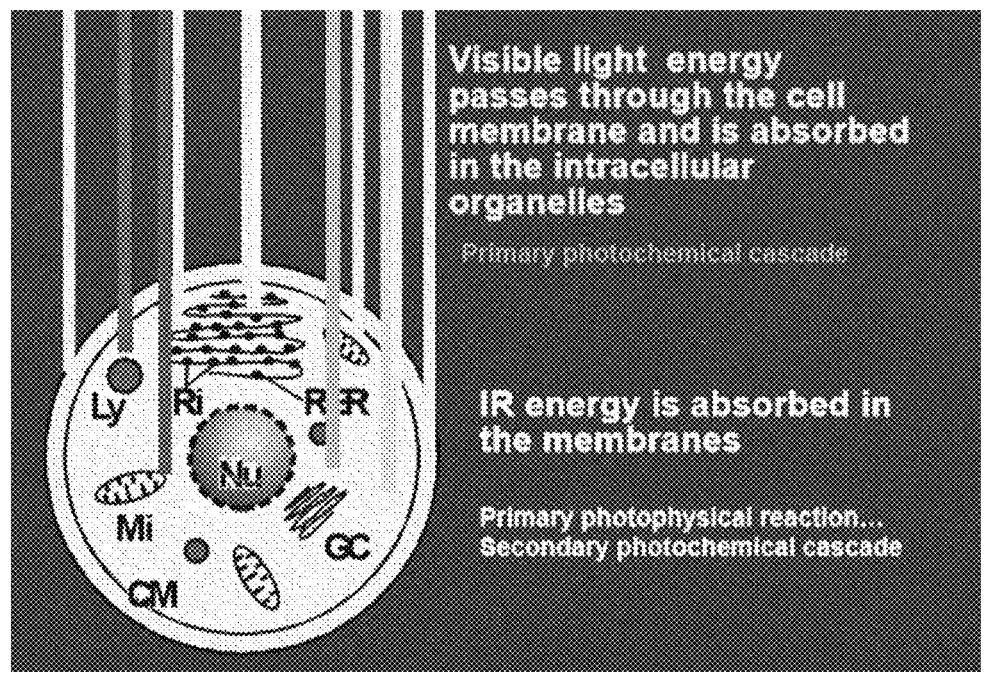

[FIG.2]
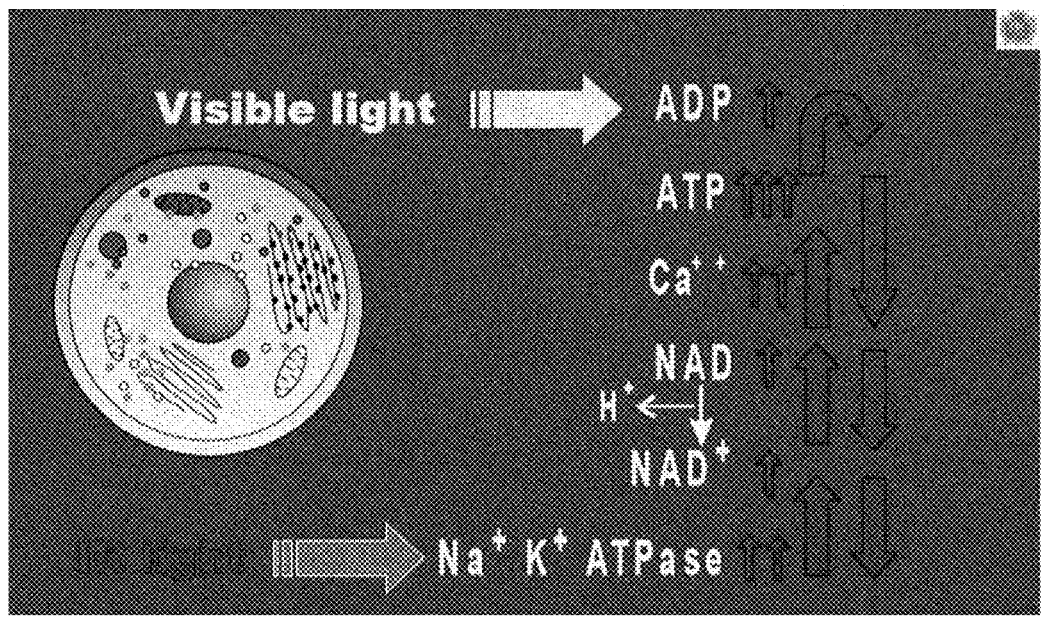

[FIG.3]
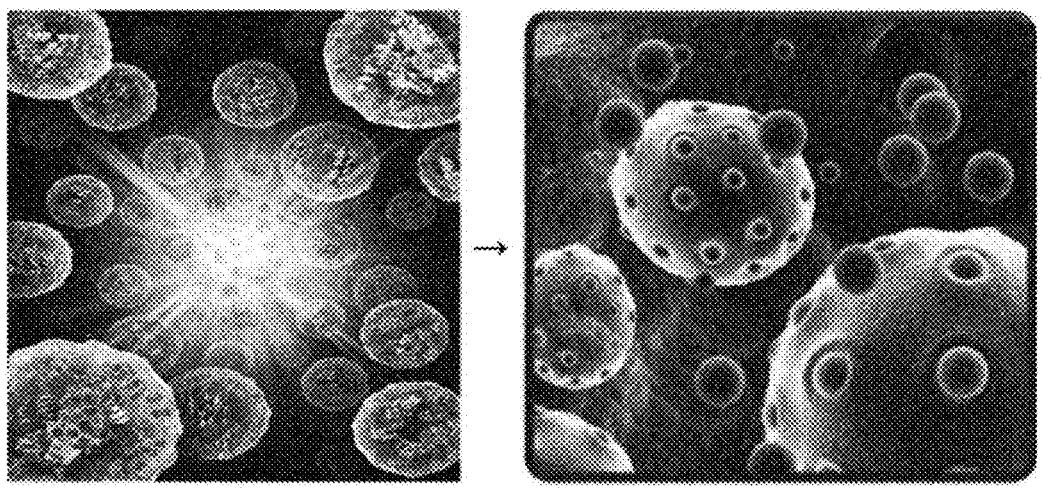

[FIG.4]
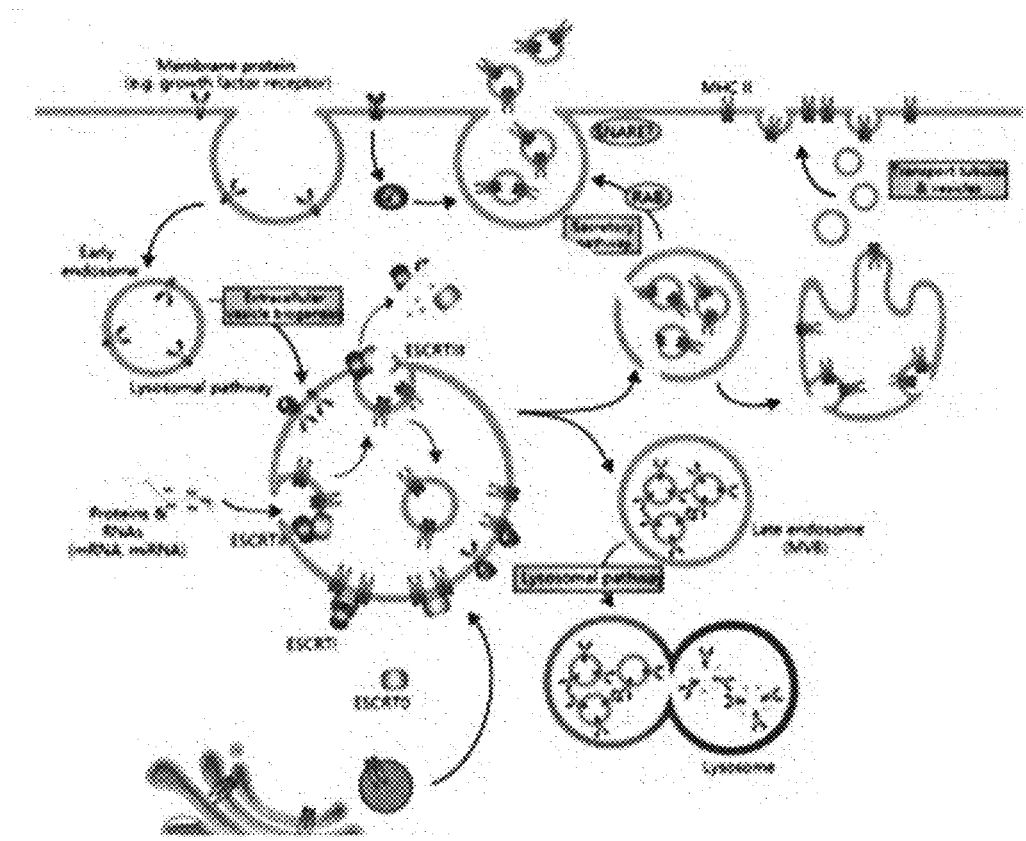
Exosomes Pathway-
Creative Diagnostics

[FIG.5]
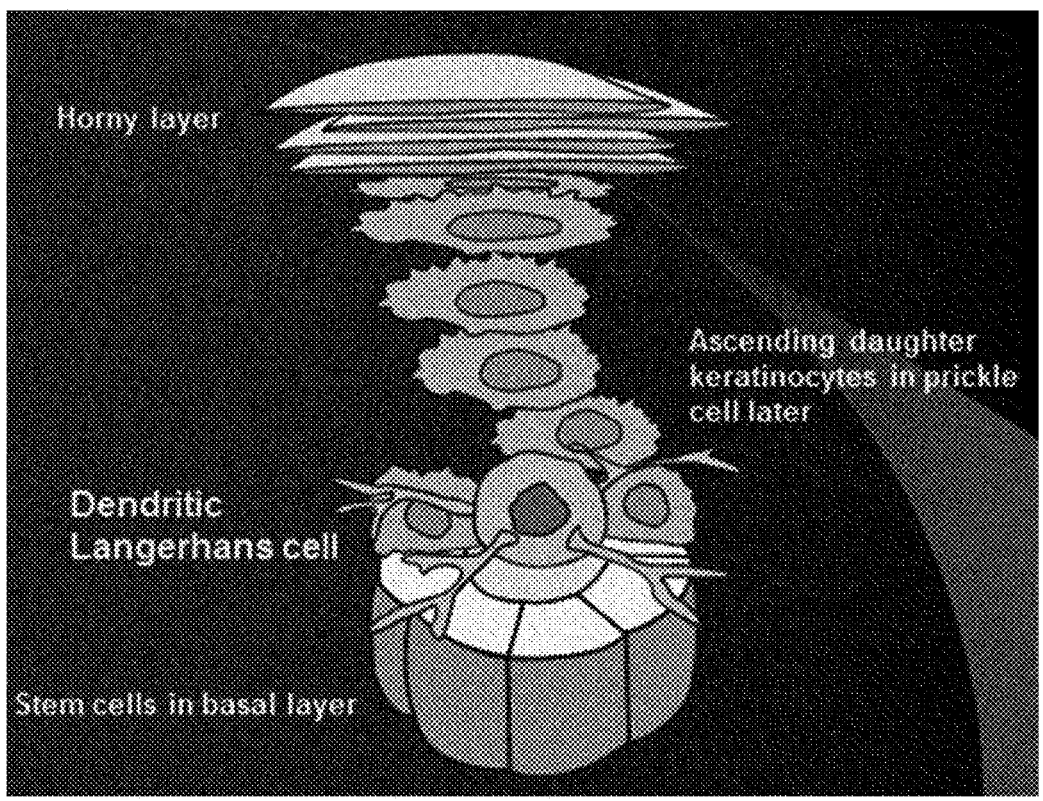

[FIG.6]
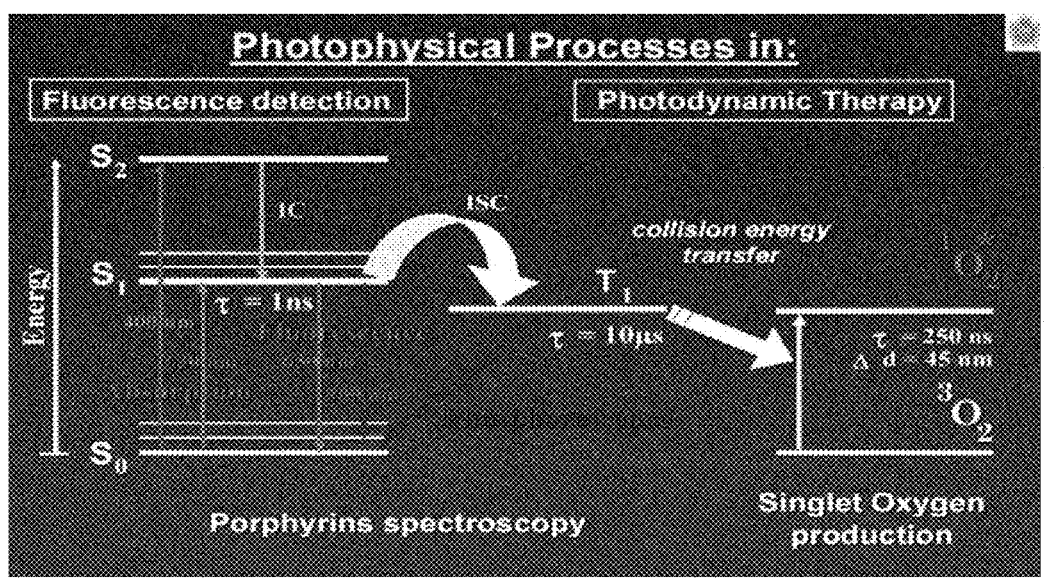

[FIG.7]
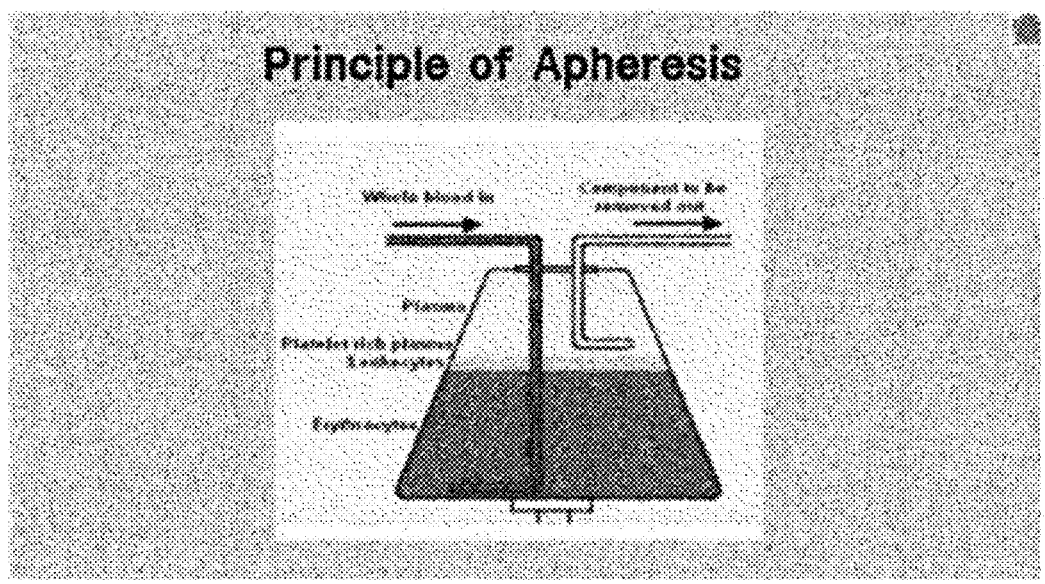

[FIG.8]
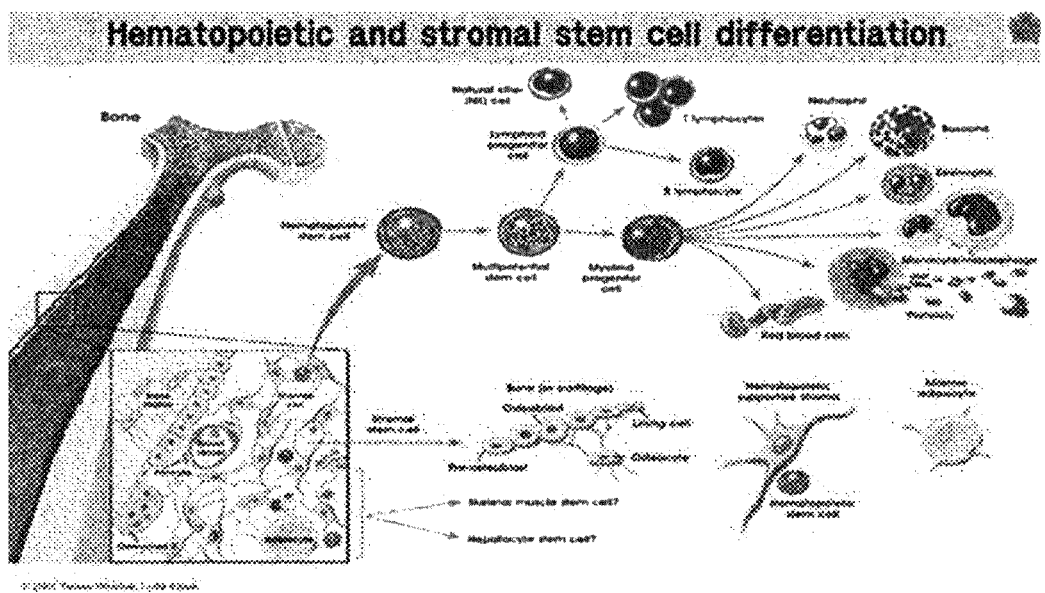

[FIG.9]

| Nominal Wavelength (nm) | Cell Types/Action Level | | | | | |
|---|---|---|---|---|---|---|
| | Mast | Neutrophil | Macrophage | Fibroblast | Fibro-Myo | Keratinocyte |
| 630–670 | ++ | + | ++ | +++ | + | +++ |
| 790 | ++ | ? | ? | ++ | ? | ? |
| 830 | +++ | +++ | +++ | + | +++ | +++ |
| 904 | − | ? | ± | − | − | ? |
| 1064 | ? | ? | ? | + | ? | ? |
| 10600 | ? | ? | ? | + | ? | ? |

PHOTOTHERAPEUTIC WAVELENGTH-SPECIFIC ACTIONS IN RAISING ACTION POTENTIALS OF SPECIFIC CELLS

[FIG.10]
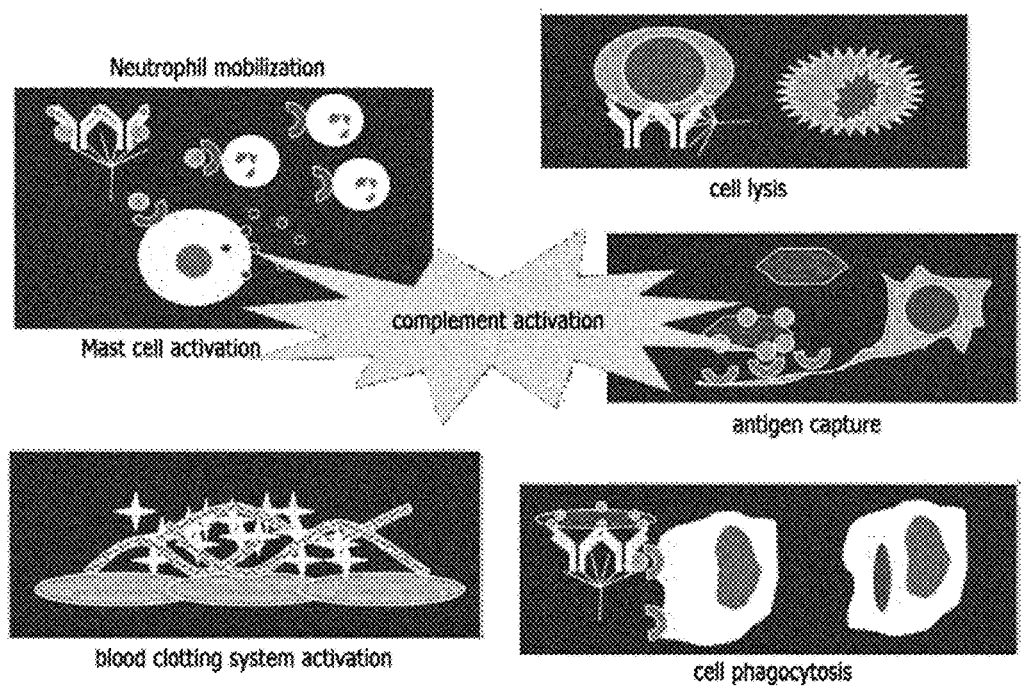

[FIG.11]
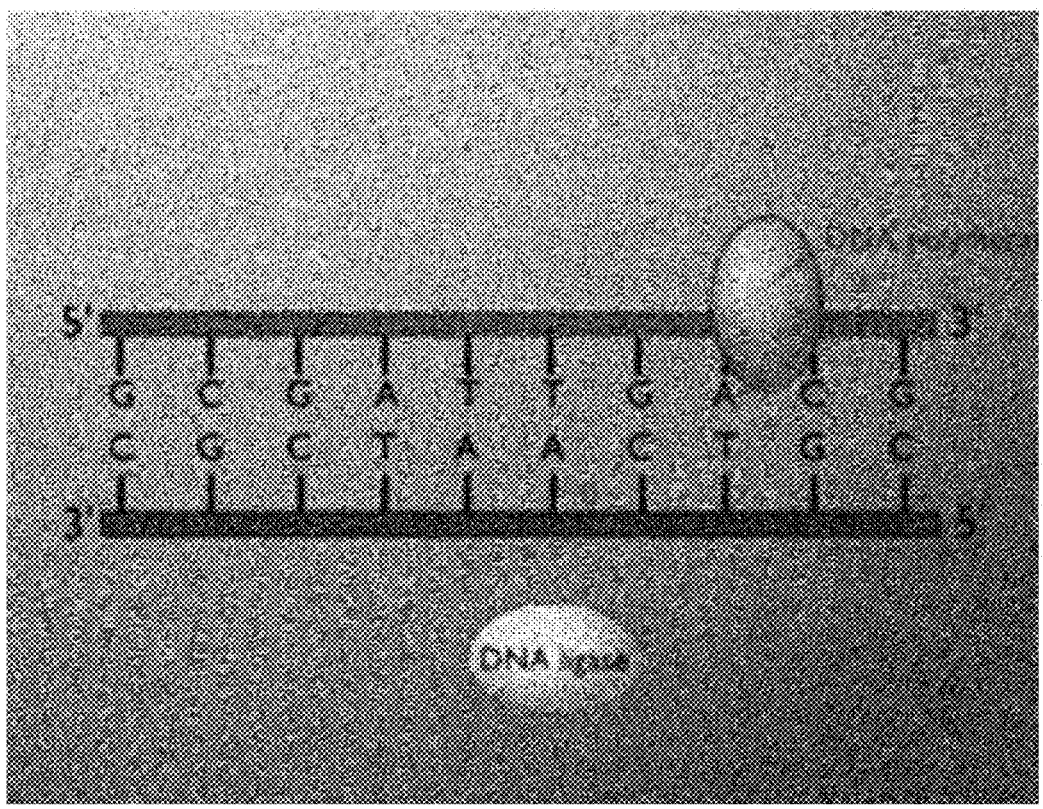

[FIG.12]
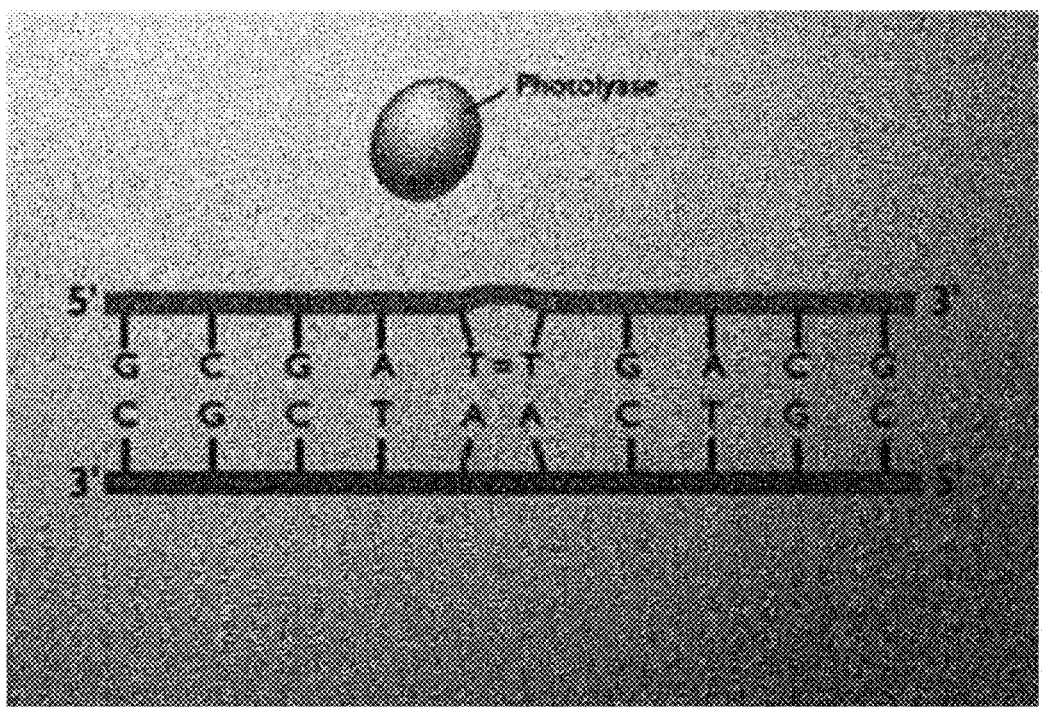

[FIG.13]
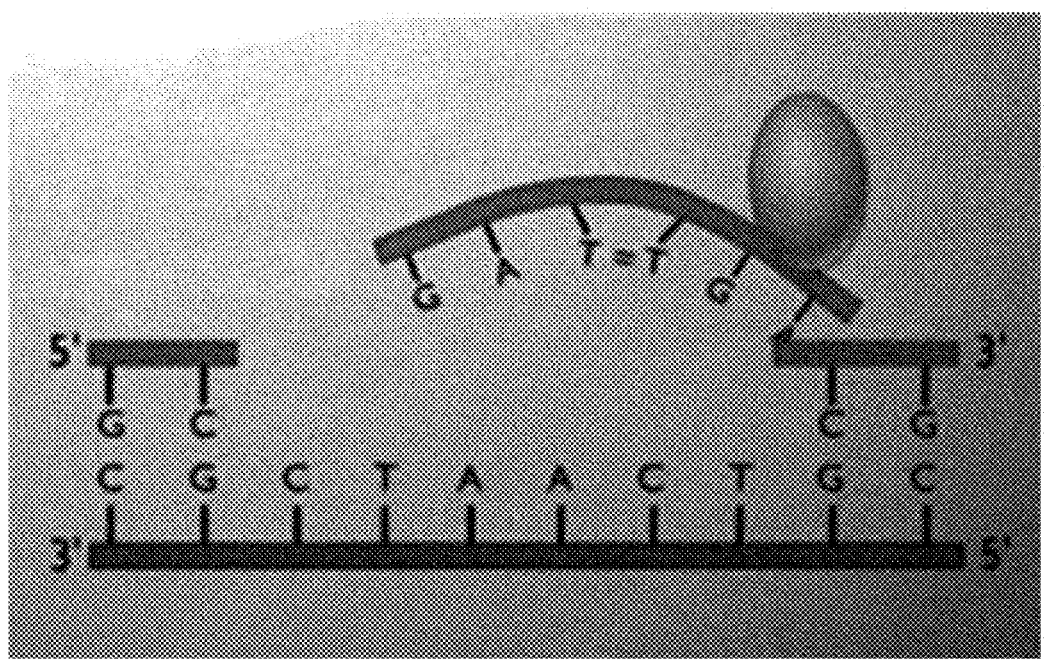

[FIG.14]
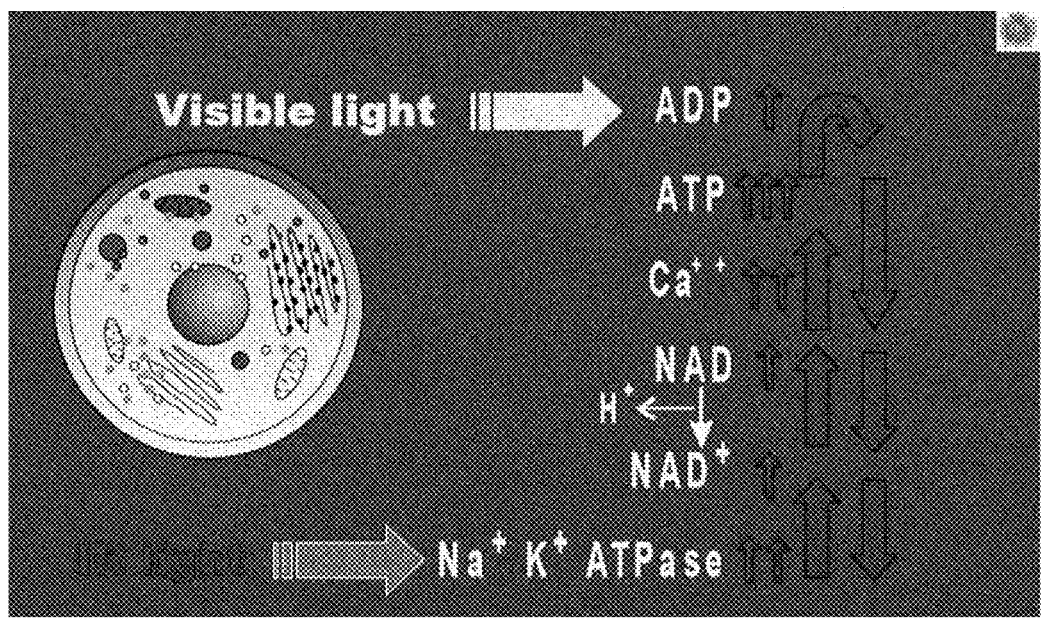

[FIG.15]
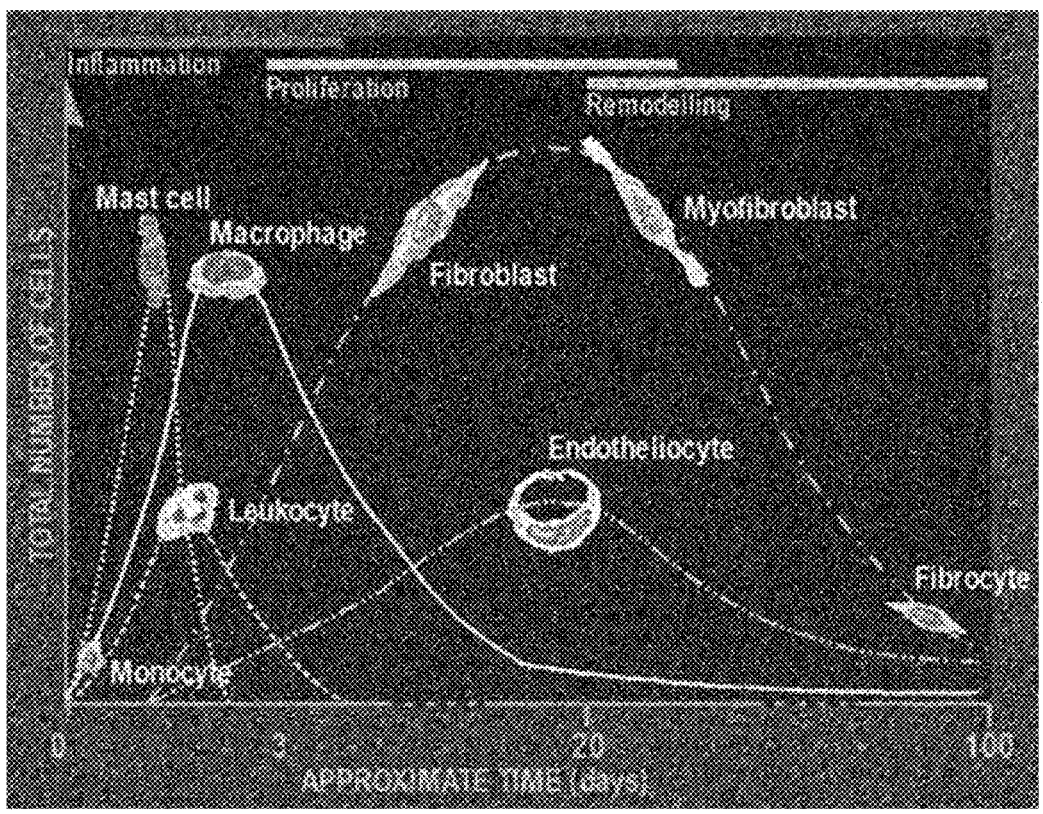

[FIG.16]
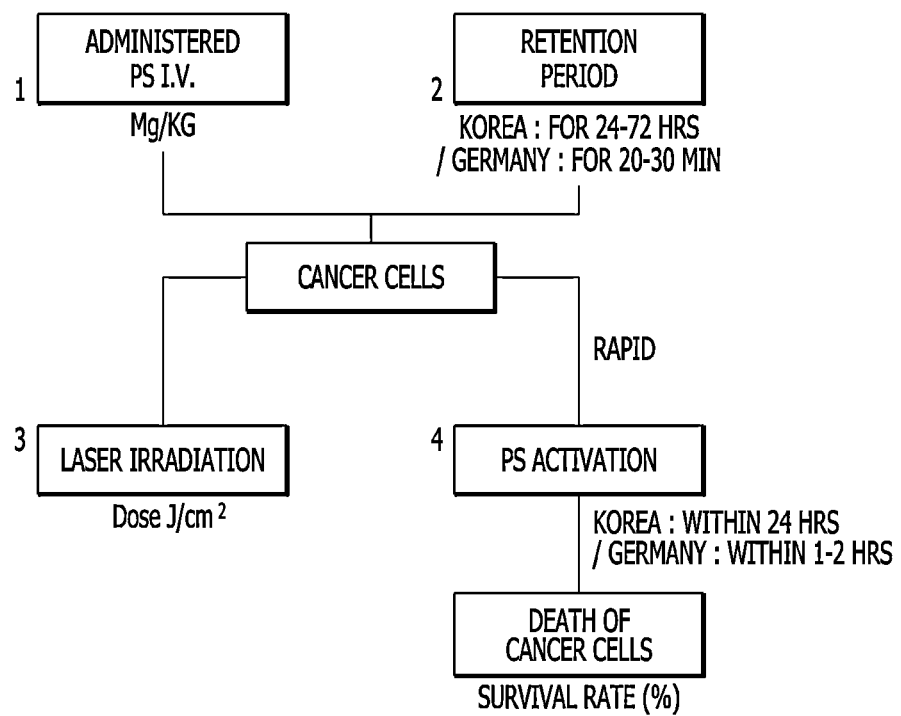

[FIG.17]
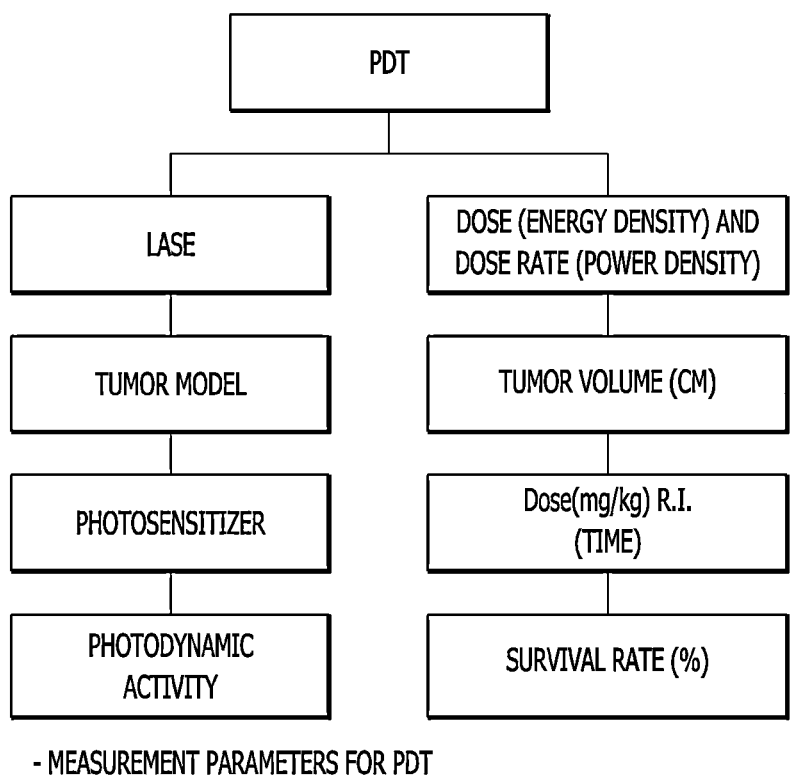
- MEASUREMENT PARAMETERS FOR PDT

[FIG.18]
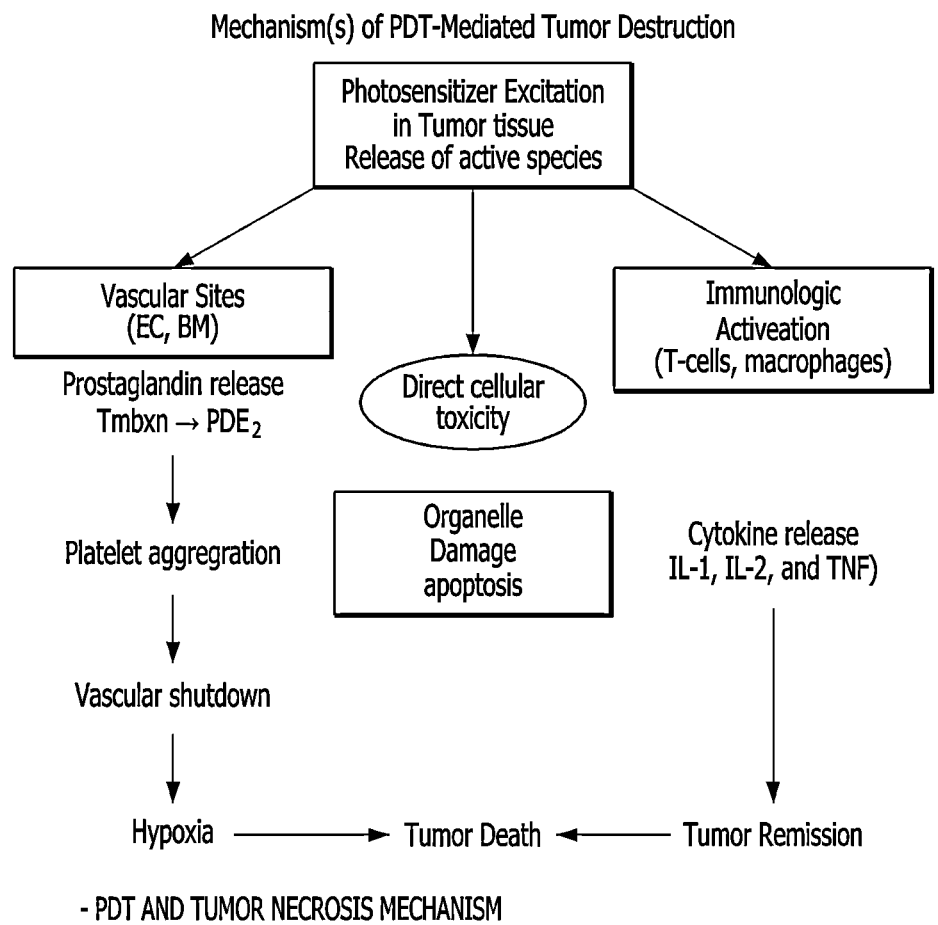

ECO-FRIENDLY SMART PHOTOSENSITIZER AND PHOTO-STEM CELL THERAPY PRODUCT COMPRISING SAME

CROSS REFERENCE TO RELATED APPLICATIONS

This application is a National Stage of International Application No. PCT/KR2020/017009 filed Nov. 26, 2020, claiming priority based on Korean Patent Application No. 10-2019-0171174 filed Dec. 19, 2019 and Korean Patent Application No. 10-2020-0101343, dated Aug. 12, 2020, the entire disclosures of which are incorporated herein by reference.

TECHNICAL FIELD

The present invention relates to an eco-friendly smart photosensitizer and a photo-stem cell therapeutic agent including the same.

BACKGROUND ART

Photodynamic therapy (PDT) is a technology of treating incurable diseases such as cancer or diseases such as acne without surgery using a photo-sensitive material (hereinafter, referred to as a "photosensitizer"). PDT has been actively studied since the beginning of the 20$^{th}$ century, and is currently used in diagnosing and treating cancer, allogeneic and autologous bone marrow transplantation, resolution of a graft-versus-host disease by photopheresis, antibiotics, treating infectious diseases such as AIDS, organ and skin transplantation, or treating arthritis or spinal muscular dystrophy. In addition, PDT is being used to enhance immunity or control and regulate an immune response, and its applications range such as regenerative medicine, biosensors and optogenetics is gradually expanding.

Particularly, PDT used in cancer treatment is a treatment that uses a principle of producing singlet oxygen or free radicals by a chemical reaction between abundant oxygen in the body and external light when light is irradiated after a photosensitizer, which is sensitive to light, is administered to the body and destroying various lesions or cancer cells by cell death induction by the singlet oxygen or free radicals.

For the photosensitizer used in the current PDT, a porphyrin derivative, chlorin, bacteriochlorin, phthalocyanine, a 5-aminolevulinic acid derivative, and porfimer sodium are known.

As the photosensitizer, a cyclic tetrapyrrole derivative not only accumulates selectively in cancer cells, but also exhibits fluorescence or phosphorescence due to the characteristics of the compound, so it can be used as a reagent for early diagnosis of tumors. In addition, since metalloporphyrin in which a metal is bound in cyclic tetrapyrrole exhibits several characteristics according to the type of the bound metal, metalloporphyrin is used as a contrast agent for magnetic resonance imaging (MRI) and applied to the early diagnosis of tumor cells such as cancer cells, the 5-aminolevulinic acid derivative, which is the most widely known photosensitizer, has advantages in that it is simple to use, is relatively easy to penetrate into the skin because of a small molecular weight, and is safe due to few side effects.

In addition, PDT has the advantages of selectively removing cancer cells while preserving normal cells, eliminating most of the risk of general anesthesia, and being easy to operate, which means performing surgery with only simple local anesthesia.

However, PDT is difficult to apply to bulky tumor cells, through which light cannot penetrate, and in particular, has been found to have a side effect of phototoxicity since a photosensitizer is slowly metabolized in the human body and remains in the body for a long time, and there is a problem in that the concentration of the photosensitizer in the tumor is low because it is difficult to accumulate in the tumor, so that it does not show an efficient therapeutic effect.

In addition, in the case of PDT, there is the inconvenience of having to live in an environment without light after the procedure due to the long half-life of the photosensitizer and the disadvantage of difficult accumulation in tumors, and for a long time other than treatment, a therapeutic compound is accumulated in the body, causing various side effects in the body. In addition, in the case of photosensitizers used for PDT, most of them are hydrophilic products, and since they are hydrophilic products which have difficulty in penetrating into the skin, they have to be treated several times over a long period of time, so it takes a lot of time for treatment.

In this regard, more specifically, according to the related art, for example, Patent Application Nos. 10-2008-0095182 (Novel photodynamic therapeutic agent using polymer derivative-photosensitizer complex) and 10-2005-0019956 (PDT using photosensitizer and chemical light), the drug itself is administered locally or drugs are combined and used for PDT. However, the former method is only possible for local treatment, and the latter method has a problem in that it is difficult to utilize polysaccharides that do not dissolve well in an organic solvent.

Particularly, it was proven at conferences and clinical trials that a porfimer sodium photosensitizer among the photosensitizers has efficacy on obstructive endobronchial cancer and esophageal cancer, and is used as a drug that has already been verified for drug efficacy and side effects. However, the porfimer sodium photosensitizer has a disadvantage of limited photosensitivity due to skin pigmentation and photosensitivity blister edema appearing as side effects in areas exposed to sunlight 30 days after treatment. Therefore, although the porfimer sodium photosensitizer can be very effectively used in PDT, its use is limited by the above-described side effects.

For these reasons, there is a demand for developing a method of improving the above-described disadvantages of the porfimer sodium photosensitizer.

DISCLOSURE

Technical Problem

The present invention is provided to solve the problems according to the related art.

Specifically, the inventors recognized that, if a phototoxic reaction caused by sunlight before and after the time of treatment can be reduced, a porfimer sodium photosensitizer can be a clinically perfect therapeutic agent, and intensive research was conducted to improve the above problems.

As a result, the inventors found that an eco-friendly smart photosensitizer can be provided as a very excellent photosensitizer in which the above problems are solved when porfimer sodium is used together with hydroxypropyl cellulose, and thus the present invention was completed.

Therefore, the present invention is directed to providing an eco-friendly smart photosensitizer that minimizes side effects and greatly improves PDT effects by using porfimer sodium and hydroxypropyl cellulose together, and a photo-stem cell therapeutic agent including the same.

Technical Solution

To solve the above problems, the present invention provides an eco-friendly smart photosensitizer including a conjugate of hydroxypropyl methylcellulose and a porfimer sodium photosensitizer.

In one embodiment of the present invention, the conjugate may be prepared by an ester bond.

In one embodiment of the present invention, the hydroxypropyl methylcellulose may be a compound represented by Formula 1 below:

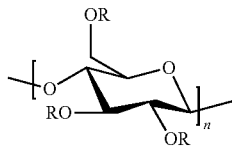

[Formula 1]

In this formula,
R is each independently hydrogen or a 2-hydroxypropyl group, and
n is a natural number from 1 to 10.

The compound represented by Formula 1 may be a compound represented by Formula 2 below:

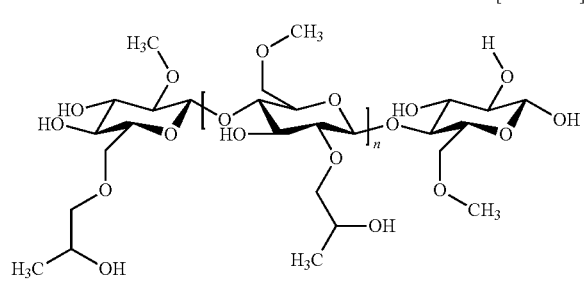

[Formula 2]

In this formula,
n is an integer from 0 to 7.

In one embodiment of the present invention, the porfimer sodium photosensitizer may be a compound represented by Formula 3 below:

In this formula,
R is each independently —CH=CH$_2$ or —CH(OH)—CH$_3$, and
n is an integer from 0 to 6.

In one embodiment of the present invention, the conjugate may not exhibit cytotoxicity during blood circulation or in normal tissue, but may be selectively targeted, accumulated and decomposed only in cancer tissue or cancer cells to produce singlet oxygen or free radicals when near-infrared wavelength light is applied, exhibiting cytotoxicity.

In one embodiment of the present invention, when the conjugate is targeted and accumulated in cancer tissue or cancer cells, the linkage between an ester bond and a polymer may be cleaved by an enzyme in vivo and fluorescence interference may be released to exhibit fluorescence.

In one embodiment of the present invention, the eco-friendly smart photosensitizer may be used as a photosensitizer fused with a target protein, an antigen-presenting cell, a stem cell-derived exosome, and a liposome.

In one embodiment of the present invention, the eco-friendly smart photosensitizer may be used as photodynamic immune anticancer therapeutic agent combined with a virus, an immune cell and a vaccine.

In one embodiment of the present invention, the eco-friendly smart photosensitizer may be used as a photodynamic immune anticancer therapeutic agent combined with an anticancer protein.

In one embodiment of the present invention, the eco-friendly smart photosensitizer may be used in treating lung cancer, gastrointestinal cancer, esophageal cancer, skin cancer, and cervical cancer.

In addition, the present invention provides a photo-stem cell therapeutic agent including the eco-friendly smart photosensitizer.

Advantageous Effects

As the eco-friendly smart photosensitizer according to the present invention uses porfimer sodium and hydroxypropyl cellulose together, an effect of minimizing side effects and greatly improving a photodynamic therapy (PDT) effect is provided.

In addition, the present invention provides a photo-stem cell therapeutic agent in which side effects are minimized and the PDT effect is greatly improved by using the smart photosensitizer.

DESCRIPTION OF DRAWINGS

FIGS. 1 to 6 are schematic diagrams illustrating the mechanism of action of a photosensitizer of the present invention.

[Formula 3]

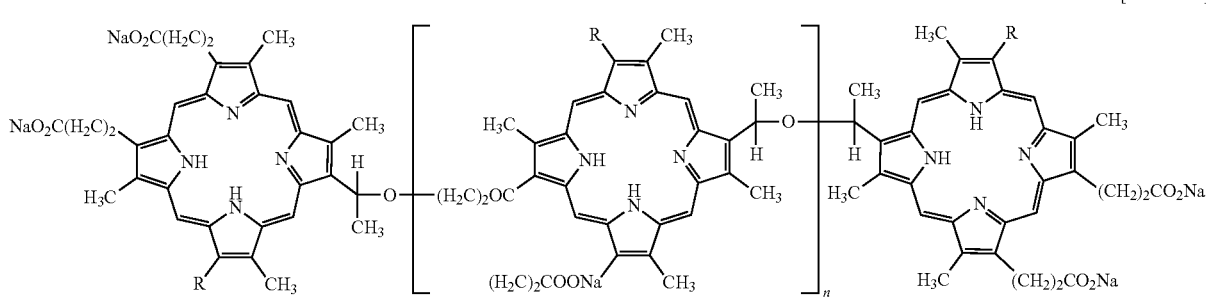

FIG. 7 shows the principle of isolating red blood cells, white blood cells, plasma, platelets, and stem cells through photodynamic extracorporeal photopheresis.

FIG. 8 is a schematic diagram illustrating the process of differentiation of bone marrow-derived blood stem cells.

FIG. 9 shows a result of photo bioregulation on stem cells, exhibiting the cell activation effect according to the wavelength of light.

FIG. 10 shows neutrophil recruitment by mast cell photostimulation instead of G-CSF, without G-CSF.

FIGS. 11 to 13 are schematic diagrams illustrating a DNA repair process by photoactivation that can be expected when a photosensitizer of the present invention and a stem cell-derived photosensitizer are used in combination.

FIG. 14 shows the $Na^+$, $K^+$, APTase, NADH, Ca, ATP flow in mitochondria and a cell membrane of cells after irradiation.

FIG. 15 shows the examples and duration of action of cells appearing in wound healing.

FIG. 16 shows the schematic diagram of the mechanism of photodynamic therapy (PDT).

FIG. 17 shows measurement parameters for PDT.

FIG. 18 shows the mechanism of tumor necrosis by PDT.

MODES OF THE INVENTION

Hereinafter, the present invention will be described in detail.

The present invention relates to an eco-friendly smart photosensitizer including a conjugate of hydroxypropyl methylcellulose and a porfimer sodium photosensitizer.

The eco-friendly smart photosensitizer of the present invention is a novel photosensitizer characterized by using hydroxypropyl cellulose, which is a raw material of pharmaceuticals, in combination with porfimer sodium, which is a conventional phototherapeutic agent.

Although the eco-friendly smart photosensitizer having an anticancer effect does not cause a reaction even when light is applied at a human body temperature, when the reaction temperature reaches 45 degrees, it emits active singlet oxygen and characteristically kills only cancer cells by a photothermal reaction. Since there is no effect just by receiving light, there is an advantage that, even when receiving sunlight, there is no fear of side effects.

The eco-friendly smart photosensitizer of the present invention is a $4^{th}$ generation innovative biopharmaceutical that can reduce the side effects of conventional chemotherapeutics, targeted anticancer agents, immunotherapeutics and photosensitizers, overcome the problems of stem cell therapy, and clinically exhibit the best effect in immunological treatment.

The eco-friendly smart photosensitizer of the present invention may be effectively used in extracorporeal photopheresis. For reference, FIG. 7 shows the principle of isolating red blood cells, white blood cells, plasma, platelets, and stem cells through photodynamic extracorporeal photopheresis.

FIGS. 1 to 6 show the mechanism of action of the photosensitizer of the present invention.

That is, as shown in FIG. 1, visible light, which is near-infrared light, is absorbed into the mitochondria of cells and stem cells. In addition, as shown in FIG. 2, the near-infrared light is absorbed by the cell membrane and involved in cell energy production, and activates cells, but conversely, in the presence of the photosensitizer of the present invention, cell death is induced by the generation of singlet oxygen. For example, as shown in FIG. 6, when the near-infrared light such as laser is irradiated, the photosensitizer of the present invention kills cancer cells by singlet oxygen generated by photothermolysis and occludes blood vessels by heat.

The photosensitizer of the present invention, as shown in FIG. 3, may be in the form of a photosensitizer anticancer agent in which a target protein, an antigen-presenting cell, a stem cell-derived exosome, a liposome, and a vaccine are fused. That is, the photosensitizer of the present invention is selectively delivered only to cancer cells as the exosome capsule-type photosensitizer shown in FIG. 3.

When organ cells except the skin in the human body and skin cells produce hormones, active materials, and nerve tissue materials, they travel to various organs such as bones, muscles and the brain via the blood. When the skin fails to do these actions due to aging, health is lost, so diagnosis and disease management through biomodulation are very important. Thanks to the development of science and technology, a new paradigm has begun in the era of treatment using stem cells and the use of a stem cell-derived network and a target protein corresponding to a courier service, and the photosensitizer of the present invention is effectively used as an anticancer agent that implements this paradigm as shown in FIGS. 1 to 6.

The porfimer sodium photosensitizer used in the present invention is a drug that has been proven to be effective on obstructive endobronchial cancer and esophageal cancer at conferences and clinical trials, and has drug efficacy and side effects that have already been verified. However, the porfimer sodium photosensitizer has a disadvantage of limited photosensitivity due to skin pigmentation and photosensitivity blister edema appearing as side effects in areas exposed to sunlight 30 days after treatment.

Therefore, porfimer sodium can be a clinically perfect novel drug if it can reduce the phototoxic reaction caused by sunlight before and after treatment time. The inventors have earnestly studied to improve the characteristics of the porfimer sodium, and consequently found that, when porfimer sodium and hydroxypropyl cellulose are used together, a very excellent photosensitizer can be provided. Thus, the present invention was completed. Both of the porfimer sodium and the hydroxypropyl cellulose are safe materials approved by the Ministry of Food and Drug Safety and clinically available.

The photosensitizer of the present invention can be used for systemic metastatic cancer, terminal cancer, or recurrent cancer, and even if necrosis occurs after a procedure, there is a realistic method for treating the necrosis (biomodulation), so it can be very useful. Particularly, when cancer metastasizes to the esophagus and lungs, the surgical method is difficult, and immunotherapy, radiotherapy and chemotherapy are difficult, so treatment with the photosensitizer of the present invention can be the only way to prolong a patient's life. In addition, the treatment with the photosensitizer of the present invention has very excellent cost-effectiveness.

The photosensitizer of the present invention, that is, the eco-friendly smart photosensitizer may be used as a photosensitizer fused with a target protein, antigen-presenting cells, an stem cell-derived exosome, and a liposome.

In addition, the eco-friendly smart photosensitizer of the present invention may be used as a photodynamic immune anticancer therapeutic agent combined with a virus, immune cells and a vaccine.

In addition, the eco-friendly smart photosensitizer of the present invention may be used as a photodynamic cancer immunotherapeutic agent combined with an anticancer protein.

In addition, the eco-friendly smart photosensitizer of the present invention may have a hair growth effect when the dose is increased or decreased only by using the photosensitizer without light, so it can be used as a hair growth agent without side effects.

FIG. 16 schematically illustrates the mechanism of PDT. As shown in FIG. 16, the photosensitizer of the present invention may be administered via a vein. Here, the photosensitizer is concentrated in target tissue such as cancer tissue over the retention period of approximately 0.3 to 72 hours. Subsequently, when the cancer tissue is irradiated with light, the photosensitizer is activated and generates singlet oxygen, causing necrosis of cancer cells.

In order to effectively perform PDT in the present invention, it is necessary to select the wavelength of a laser system and a dose, which is an energy density, well. The criteria for selecting a wavelength band are closely related to higher photoactivation as the relative absorption with the photosensitizer is higher and the light penetration depth of living tissue. FIG. 16 shows the measurement parameters for the photodynamic treatment. The mechanism of tumor necrosis by PDT of the present invention is shown in FIG. 19.

The photosensitizer of the present invention may be used along with graphene. Graphene is an important DNA exon and intron biocomputing IoT material which is used for a smart artificial skin sensor and cell sensor, which do not require a battery. Graphene is a superconducting material that can communicate with an external computer without external power, can move by a magnetic force, is easy to control from the outside, and is useful for advanced bioindustry, and is known as a dream material because its infinite utility value as a bio-IoT material in developing a future computer, a bio-computer. In addition, it is also a dream material that is widely used as a material for bio and computer secondary batteries.

When the photosensitizer of the present invention is used in a fusion type with graphene, the pathway of cell activity can be known. In addition, the fusion of graphene and the photosensitizer of the present invention is used for the death of cancer cells and the removal of cancer tissue with a small dose. According to the photodynamic therapy (PDT) using graphene, it is possible to remove cancer cells, control stem cell differentiation, and treat dementia or Parkinson's disease, and since graphene also serves as a microrobot in vivo, it enables drug delivery and stem cell delivery to an appropriate location when combined with a magnetic force.

Since graphene is a metal, it can be induced with a magnetic field in an area requiring stem cell treatment, and may destroy cancer cells by delivering an LED or ultrasound from the outside as well as the inside. Therefore, when graphene is used along with the photosensitizer of the present invention (e.g., used by forming a complex), it can be used as a 4th generation photosensitizer, and it is expected that commercialization of parallel use of the photosensitizer of the present invention with a stem cell therapeutic agent will be commercialized in earnest after the Stem Cell Apoptosis Act, which will be implemented on Aug. 28, 2020.

A photoactivation-induced stem cell-derived photosensitizer can manufacture various photo stems using 5-aminolevulinic acid, which is a component of hemoglobin, and a bio-photosensitizing material. When the photosensitizer or graphene photosensitizer of the present invention is used in combination with the stem cell-derived photosensitizer, it is possible to treat cancer and incurable diseases using various wavelengths. In addition, during the treatment with stem cells, it is possible to prevent unwanted malignancy, and perform the function of an eco-friendly smart photosensitizer that can control side effects. FIGS. 11 to 13 are schematic diagrams showing the DNA repair process by photoactivation that can be expected when the photosensitizer of the present invention and the stem cell-derived photosensitizer are used in combination.

The type of medical light that can be used in the present invention may be a semiconductor laser diode laser and the like, and specifically, light exemplified in the following table may be used.

| Laser type | Wavelength range | Output | Use |
|---|---|---|---|
| Dye (pumping excimers with Argon-ion) | 631 nm (red) | Continuous type, 3-4 W | photoactive (tumor treatment) nevus flammeus angiectasis, blood vessel spots hot flashes selective coagulation using endoscope |
| Argon-ion | 488 (blue-green) | Continuous type, up to 10 W | photocoagulation (retina), inosculation, vaporization eye surgery (retina) laser scope for surgery laser endoscope, coagulator cartilage incision and hole in nose removal of moles, blemishes, and tattoos |
| Argon Fluoride | 192 nm (UV) | Pulse type, up to average 10 W per pulse | cutting, melting selective cell condensation |
| Kripton Fluoride | 248 nm (UV) | | other argon laser applications myopia correction |
| Nd:YAG | 1.064 μm (IR) | Continuous type, up to 60-100 W | photocoagulation, vaporization, hanger, hole laser scope for surgery laser endoscope, coagulator urology lithotripsy tattoos, black moles |

-continued

| | | | |
|---|---|---|---|
| $CO_2$ | 10.6 μm (IR) | Continuous type, up to 80 W | tissue vaporization, incision pigmented nevus, senile plaque laser scope for surgery warts, strawberry nose, benign tumors |
| Q-Switched Ruby | 694.3 nm | Pulse type, up to 0.03-100 J per pulse | removal of tooth decay, tartar for dental use, such as oral tumors lentigo, freckles, melasma, tattoos Ota's nevus |
| Diode | 633 nm | 90-900 $mW/cm^2$ per pulse | PDT PDD |
| Diode | 830 nm | 60-1000 $mW/cm^2$ per pulse | PDT LLLT |

| | NO | Lamp | RED | BLUE | IR | GREEN | YELLOW | Combined |
|---|---|---|---|---|---|---|---|---|
| Input | Voltage | | | | 110-240 V | | | |
| | Frequency | | | | 50/60 Hz | | | |
| | power | | | | 1.0 KW | | | |
| Output | Lamp number | | 2400 | 1500 | 800 | 100 | 1040 | RED 700 IR 500 |
| | Total output | | 80 W ± 8 W | 46 W ± 4 W | 46 W ± 8 W | 8 W ± 2 W | 8 W ± 2 W | 10.5 W ± 2 W 15.5 W ± 2 W |
| | Density (max) | | 110 $mW/cm^2$ | 60 $mW/cm^2$ | 60 $mW/cm^2$ | 10 $mW/cm^2$ | 10 $mW/cm^2$ | 25 mW 20 mW |
| | Wavelength length (nm) | | 635 ± 6 nm | 4205 ± 5 nm | 830 ± 5 nm | 530 ± 5 nm | 585 ± 5 nm | 635 ± 6 nm 830 ± 5 nm |
| | Wavelength width (nm) | | 20 ± 3 nm | 20 ± 3 nm | 30 ± 5 nm | 20 ± 5 nm | 20 ± 5 nm | 20 ± 3 nm 30 ± 5 nm |
| | Standard dose ($J/cm^2$) | | 132 $J/cm^2$ | 72 $J/cm^2$ | 72 $J/cm^2$ | 12 $J/cm^2$ | 12 $J/cm^2$ | 30 $J/cm^2$ 24 $J/cm^2$ |
| | Application time | | 20 min | 20 min | 20 min | 20 min | 20 min | 20 min |
| | Dose region | | 1-264 $J/cm^2$ | 1-144 $J/cm^2$ | 1-144 $J/cm^2$ | 1-24 $J/cm^2$ | 1-24 $J/cm^2$ | 1-60 $J/cm^2$ 1-48 $J/cm^2$ |
| Lamp panel | Total (L × W) | | | | 320-410 mm | | | |
| | Effective (L × W) | | | | 190-410 mm | | | |
| | 1 region | | | | 190-82 nm | | | |

The wavelength of light that can be used with the photosensitizer of the present invention is preferably 630 to 830 nm. The light with this range of wavelength may be effectively used in PDT and stem cell-induced activation.

For the effective application of the photosensitizer of the present invention, laser light may be used, and such laser light may be applied using an optical fiber. To apply laser light to an affected area during a PDT procedure, various forms of optical fiber catheters are used depending on the structure and shape of an organ. When divided by type, the photosensitizer includes a direct type, a microlens type that forms a round-shaped light spot, an interstitial cylindrical type that is used by directly piercing tumor tissue, and a vascular type that is directly inserted into a blood vessel. Recently, each manufacturer is developing a photosensitizer according to the location or shape of a tumor in order to increase the efficiency of light transmission. The diameter of an optical fiber is usually less than 2 mm, so it can be manufactured to be easily applied to a common endoscope. Examples of types of optical fibers applicable to the present invention are as follows:

① Direct type: Used to control the intensity of light together with a dosimetry sensor when calibrating a light dose, and used as a therapeutic catheter when a lesion is very small.

② Microlens type: Having various sizes of light spots according to the focusing ability of a lens. An optical fiber that can form circular spots with a diameter of 2.5 to 6 cm, formed by various types of lenses by each company, and spots with a diameter of 2 to 5 cm, formed by a frontal light distributor, and thus is suitable for a case where the tumor site is widely spread.

③ Cylindrical type: Most frequently used through endoscopy because of being suitable for tumors on the organ wall (lung, esophagus, vocal cords, stomach, etc.) since light comes out in the radial direction along the length of a tip.

There are 1, 2 and 3-cm tips, and the tip may be manufactured up to 10 cm depending on the order of a client by a certain company. Recently, it is highly effective in treating superficial tumors on the wall of the oral cavity, bronchus or esophagus by blocking one side of a cylinder to reflect light only to the opposite side.

④ Balloon type: Able to apply a uniform amount of light suitable for the structure of the kidney, brain tumor bed, uterus, and bronchus in the lung at one time by equipping a balloon and fitting it to the morphology in order to evenly illuminate light to a larger area.

⑤ Interstitial type: In the case of a solid cancer with a considerably large tumor, an irradiation method is ineffective when treating superficial tumors. Therefore, it is possible to effectively treat a tumor by directly inserting an optical fiber into the center of an affected area, so that light is irradiated in the entire space direction. The basic shape is similar to the cylindrical type, and a tip is made of metal, so it serves as a needle.

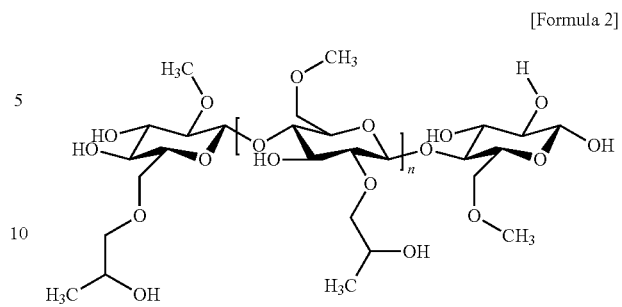

[Formula 2]

In this formula, n is an integer from 0 to 7, and preferably, a natural number from 2 to 4.

The porfimer sodium photosensitizer may be a compound represented by Formula 3 below:

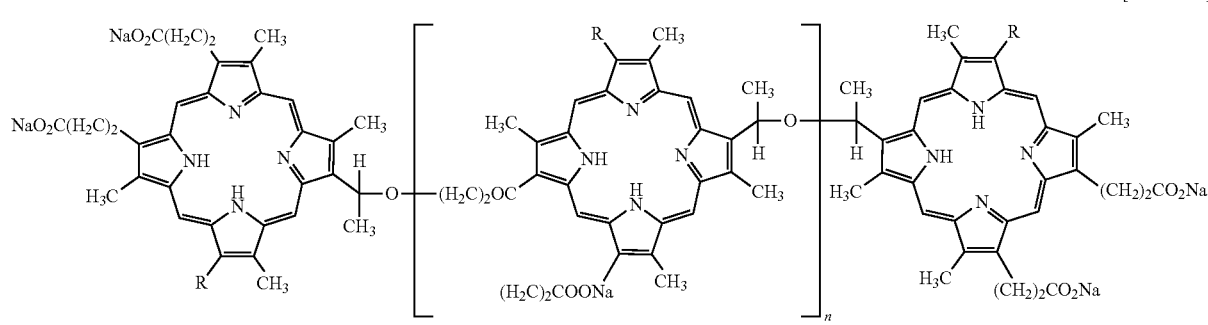

[Formula 3]

⑥ Diagnostic Light Distributor

In addition, a multi-channel optical fiber system that can diagnose a cancer site, the degree of the accumulation of a photosensitizer, and a PDT reaction using fluorescence may be used.

In the photosensitizer of the present invention, the conjugate of the hydroxypropyl methylcellulose and the porfimer sodium photosensitizer may be prepared by an ester bond.

The hydroxypropyl methylcellulose may be a compound represented by Formula 1 below:

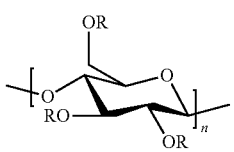

[Formula 1]

In this formula,

R is each independently hydrogen or a 2-hydroxypropyl group, and n is a natural number from 1 to 10.

In addition, the compound represented by Formula 1 may be, for example, an oligomer represented by Formula 2 below:

In this formula,

R is each independently —CH=CH$_2$ or —CH(OH)—CH$_3$, and n is an integer from 0 to 6, and preferably a natural number from 2 to 4.

As one example of the photosensitizer of the present invention, an ester conjugate of the hydroxypropyl methylcellulose of Formula 2 and the porfimer sodium photosensitizer of Formula 3 may be used, and the ester conjugate may be formed by the linkage between a hydroxyl group of the hydroxypropyl methylcellulose of Compound 2 and a sodium carboxylate group included in the porfimer sodium of Compound 3.

The ester conjugate may have a weight average molecular weight of 10,000 to 50,000 g/mol, and preferably 12,000 to 30,000 g/mol.

The compound of Formula 2 and the compound of Formula 3 may be reacted in a molar ratio of 7:1 to 2:1, preferably, 5:1 to 2:1, and more preferably, 5:1.

In the present invention, the ester conjugate of the hydroxypropyl methylcellulose of Formula 2 and the porfimer sodium photosensitizer of Formula 3 is as follows. By the ester reaction between an OH group of Formula 2 and a —COONa group of the porfimer sodium of Formula 3, an ester conjugate is formed as follows.

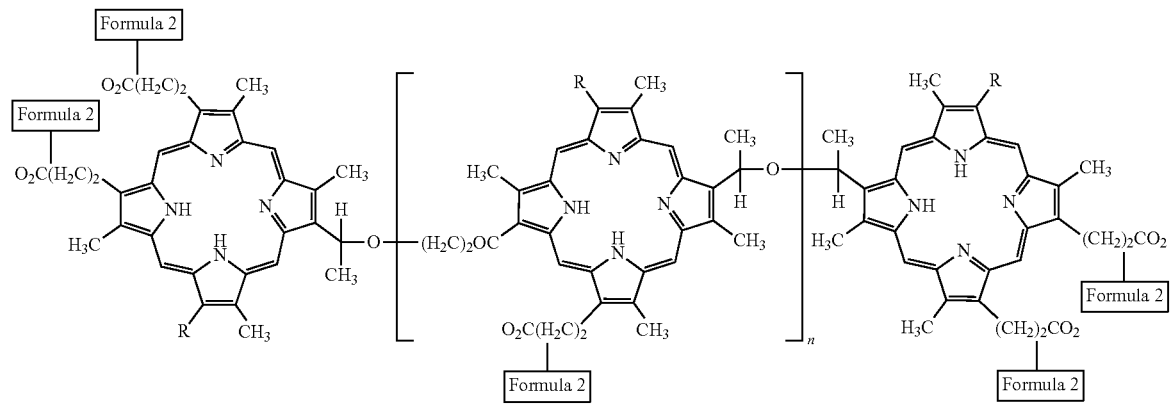

The eco-friendly smart photosensitizer of the present invention does not exhibit cytotoxicity during blood circulation or in normal tissue, and is selectively targeted, accumulated and decomposed in cancer tissue or cancer cells, thereby producing singlet oxygen or free radicals when light with a near-infrared wavelength is applied and exhibits cytotoxicity.

When the eco-friendly smart photosensitizer is targeted and accumulated in cancer tissue or cancer cells, the linkage between an ester bond and a polymer may be cleaved by an enzyme in vivo and fluorescence interference may be released to exhibit fluorescence.

The eco-friendly smart photosensitizer may stably form a nano-scale self-assembly, that is, a nanogel or nanosphere, in an aqueous system through the balance between the hydroxypropyl methylcellulose and the porfimer sodium.

Hereinafter, the present invention will be described in further detail with reference to examples below. However, the following examples are provided to illustrate the present invention is further detail, and the scope of the present invention is not limited by the following examples. The following examples may be suitably modified or altered by those of ordinary skill in the art within the scope of the present invention.

Example 1: Preparation of Photosensitizer for Photodynamic Diagnosis or Therapy 10 mol of hydroxypropyl methylcellulose represented by Formula 2 below was dissolved in 100 mL of DMSO, which is an organic solvent, from which moisture was removed.

In addition, 2.5 mol of porfimer sodium represented by Formula 3 below as a photosensitizer was sufficiently dissolved in 30 mL of DMSO.

After the porfimer sodium photosensitizer solution was added dropwise to the solution in which the hydroxypropyl methylcellulose was dissolved and while mixing well, an ester binding reaction was sufficiently performed for approximately 48 hours, thereby obtaining an ester compound having a weight average molecular weight of 13,500 g/mol. Afterward, the resulting compound was lyophilized and stored.

[Formula 2]

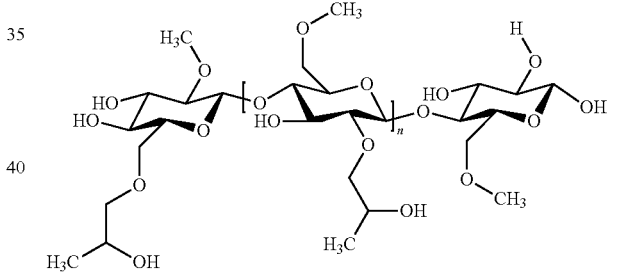

In this formula,
n is 3.

[Formula 3]

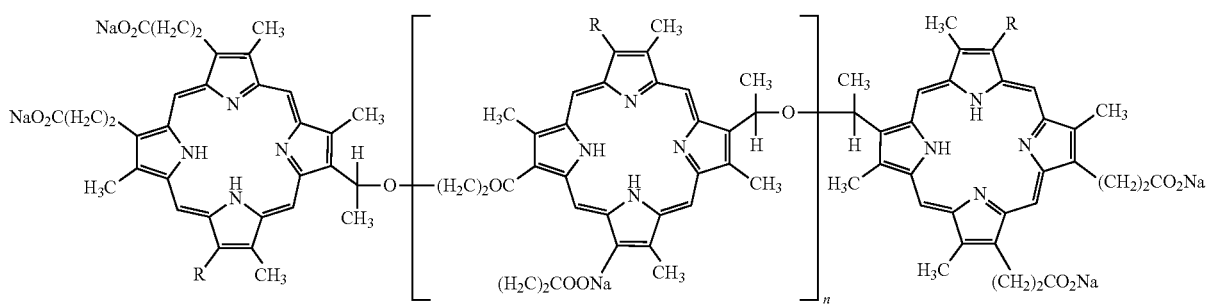

In Formula 3,
R is —CH(OH)—CH$_3$, and
n is 3.

Experimental Example 1: Analysis of Characteristics of Nanosphere (1) Measurement of Size and Shape of Microsphere Three biocompatible material samples in which the hydroxypropyl methylcellulose prepared in Example 1 was bonded to porfimer sodium by an ester bond were dissolved at 1 mg/ml, and their sizes were measured using dynamic light scattering (DLS). Here, to measure an exact size, the resulting solution was diluted with 0.1M NaCl, and its size was measured. As a result, it was seen that the diameters of the nanospheres are distributed in a range of approximately 30 to 442 nm.

(2) Confirmation of Presence of Fluorescence Interference

A biocompatible material sample in which the hydroxypropyl methylcellulose obtained in Example 1 was bonded to porfimer sodium by an ester bond was dissolved in DMSO or PBS at various concentrations, and then a fluorescence phenomenon was confirmed using a KODAK image station and a spectrofluorophotometer. It was shown that, when measured in a wavelength range of 600 to 750 nm, the intensity and image of fluorescence are differently shown according to a concentration in the organic solvent phase (A), that is, DMSO, but self-optical interference occurs in the PBS phase (B) and significant fluorescence is not shown and not affected by the concentration. It is considered that this is because the biocompatible material sample in which hydroxypropyl methylcellulose was bonded to porfimer sodium by an ester bond does not form microspheres in an organic solvent, leading to no fluorescence interference, but forms nanospheres in PBS, leading to perfect fluorescence interference. This result shows that, among the biocompatible material samples, nanospheres not accumulated in cancer cells by PDT do not exhibit cytotoxicity, so they can be stably used in the body.

(3) Evaluation of Singlet Oxygen Production Ability of Nanosphere

To verify the usability of the biocompatible material sample in which the hydroxypropyl methylcellulose of Example 1 was bonded to porfimer sodium by an ester bond as a photodynamic diagnosis or therapeutic agent, singlet oxygen production ability according to laser irradiation was measured and compared with unmodified photosensitizer porfimer sodium. First, the biocompatible material sample in which the hydroxypropyl methylcellulose of Example 1 was bonded to porfimer sodium by an ester bond and unmodified porfimer sodium were dissolved in 2 mL each of DMF and PBS (Pheo-A 1.5 μg/ml), a small amount of 9,10-dimethylanthracene that can detect singlet oxygen was added to adjust a concentration to 20 μg/ml. By using laser with a wavelength of 630 nm known to produce singlet oxygen from porfimer sodium, laser was irradiated at intervals of 40 seconds, and fluorescence was measured at Ex 360 nm and Em 380 to 550 nm using a spectrofluorophotometer.

As a result of the experiment, it was confirmed that the biocompatible material sample in which the hydroxypropyl methylcellulose of Example 1 of the present invention was bonded to porfimer sodium by an ester bond can produce almost the same singlet oxygen as the unmodified porfimer sodium. Accordingly, it can be seen that the nanospheres of the present invention can kill cancer cells through the generation of singlet oxygen in target cells (cancer cells).

(4) Confirmation of Location of Nanosphere in Cells

In order to observe cancer cell targeting of nanospheres of the biocompatible material sample in which the hydroxypropyl methylcellulose of Example 1 was bonded to porfimer sodium by an ester bond, that is, the accumulation location and accumulation rate in cancer cells, HeLa cells (1×10$^5$ cells) were treated with each of 1.25 μg/ml of the nanospheres of the biocompatible material sample in which the hydroxypropyl methylcellulose prepared in Example 1 was bonded to porfimer sodium by an ester bond and 1.25 μg/ml of unmodified porfimer sodium as a control and then the location in cells over time was observed using a confocal microscope.

As a result, it was shown that the nanospheres of the biocompatible material sample in which the hydroxypropyl methylcellulose according to the present invention was bonded to porfimer sodium by an ester bond and unmodified porfimer sodium are located at different sites in cells.

Therefore, from the above result, it can be seen that, in the case of cancer cells, the nanospheres of the biocompatible material sample in which the hydroxypropyl methylcellulose of Example 1 is bonded to porfimer sodium by an ester bond and the conventional photosensitizer porfimer sodium are absorbed into cells by different mechanisms. Furthermore, it can be seen that, compared to unmodified porfimer sodium, the nanospheres of the biocompatible material sample in which the hydroxypropyl methylcellulose of Example 1 is bonded to porfimer sodium by an ester bond of the present invention are much more accumulated in cancer cells.

(5) Experiment for Confirming the Presence of Cancer Cell Targeting Properties

To identify the absorption mechanism of the biocompatible material sample in which the hydroxypropyl methylcellulose of Example 1 is bonded to porfimer sodium by an ester bond, prepared according to the present invention in HeLa cells, the degree of intracellular uptake was measured using a flow cytometer when HeLa cells were treated with the sample of the present invention along with hydroxypropyl methylcellulose (A), when HeLa cells were treated with only the sample of the present invention (B), or when HeLa cells were treated with only hydroxypropyl methylcellulose (C). As a result, compared to when HeLa cells were treated with the sample of the present invention along with hydroxypropyl methylcellulose (A), when HeLa cells were treated with only the sample of the present invention (B), a phenomenon in which cells absorb nanospheres better was shown. Accordingly, it can be seen that hydroxypropyl methylcellulose has a competitive inhibitory action on the sample of the present invention, and it can be confirmed that the sample of the present invention is absorbed into cells by a hydroxypropyl methylcellulose receptor.

(6) Experiment for Measuring Release of Fluorescence Interference by Enzymatic Action of Cancer Cells As shown in Experimental Example (3), 1×10$^4$ HeLa cells were cultured in a 96-well plate, and treated with the nanospheres of the present invention at each concentration (need to confirm a specific concentration), and then a fluorescence phenomenon was observed using a KODAK image station. Here, as a control, a HeLa cell-free culture solution, treated with the nanospheres of the present invention, was used.

As the result of the experiment, it can be observed that, while fluorescence interference was not released in wells containing the HeLa cell-free general culture solution, in the wells containing the HeLa cell-containing culture solution, fluorescence interference is released with the passage of incubation time. In addition, when the ester bond was hydrolyzed by treating the nanospheres of the present invention with esterase, it can be confirmed that the fluorescence interference was released in proportion to the concentration of esterase treated and the incubation time.

Accordingly, from the above result, the inventors have found that, when the nanospheres prepared in the present invention are targeted and accumulated in cancer cells, fluorescence interference is released by the enzymatic action of cancer cells, and then when near-infrared wavelength light is irradiated, cancer can be treated by killing cancer cells using a photosensitizer.

(7) Experiment for Evaluating Cytotoxicity

A cytotoxicity test was performed on nanospheres according to the present invention prepared in Example 1. First, HeLa cells as cancer cells were incubated in an RPMI1640 medium supplemented with 10% FBS and 1% penicillin at 5% $CO_2$ 37° C. Subsequently, in the cytotoxicity test, the incubated HeLa cells were seeded in a 96-well plate at $1 \times 10^4$ cells/well and incubated for 24 hours, and the next day, the nanospheres prepared in Example 1 of the present invention (nanospheres to which 1.25 mg of a photosensitizer was added) were diluted by concentration and added to each well at 100 µl. Afterward, the nanospheres were further incubated in an incubator for 12 hours so as to act on the cells, and light in a near-infrared wavelength band (630 nm) was irradiated at a dose of 1.2 $J/cm^2$. Here, cells that are treated with the sample at the same concentration for the same treatment time but not irradiated with the light were used as a control and compared with the experimental group. Afterward, the cells were incubated again for a day in an incubator.

Finally, an MTT reagent (3-(4,5-dimethylthiazol-2yl)-2,5-diphenyl-2H-tetrazolium bromide) was added to the completely-cultured cells at 20 µl, and incubated again for 3 to 4 hours. After 4 hours, both of the medium and the MTT reagent were removed, and 150 µl of DMSO was added to dissolve bluish-purple non-aqueous formazan formed in cells. Afterward, by measuring the absorbance at 595 nm using an ELIZA analyzer, the amount of formazan formed was compared to confirm the viability of cells and the cytotoxicity of the complex.

As result of the experiment, after the nanospheres prepared in Example 1 of the present invention were added to cells and incubated, when near-infrared radiation was not applied, cell death did not occur regardless of irradiation time, whereas when near-infrared radiation was applied, cell death occurred and cell viability decreased in proportion to irradiation time.

In the above, the present invention has been described with reference to preferred examples. It will be understood by those of ordinary skill in the art that the present invention can be implemented in modified forms without departing from the essential characteristics of the present invention. Therefore, the disclosed embodiments should be considered in a descriptive aspect, rather than a limiting aspect. The scope of the present invention is shown in the claims rather than the foregoing description, and all differences within the equivalent range thereto will be construed as being included in the present invention.

Modes for carrying out the present invention have been described together in the above best mode for carrying out the invention.

INDUSTRIAL APPLICABILITY

The present invention relates to an eco-friendly smart photosensitizer and a photo-stem cell therapeutic agent including the same, and provides an effect of minimizing side effects and greatly improving a PDT effect, thereby exhibiting industrial availability.

The invention claimed is:

1. A photosensitizer, comprising:
a conjugate of hydroxypropyl methylcellulose and a porfimer sodium photosensitizer,
wherein the hydroxypropyl methylcellulose is represented by Formula 2 below,
the porfimer sodium photosensitizer is represented by Formula 3 below, and
the hydroxypropyl methylcellulose and the porfimer sodium photosensitizer form a conjugate by an ester bond:

[Formula 2]

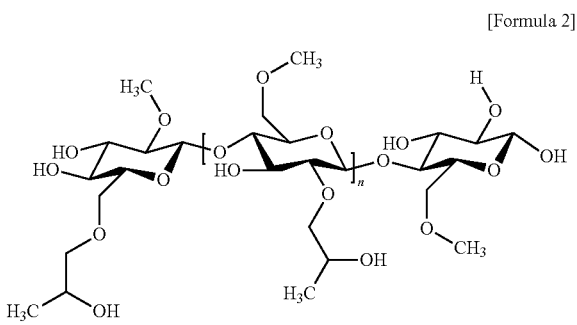

In Formula 2,
n is an integer from 0 to 7

[Formula 3]

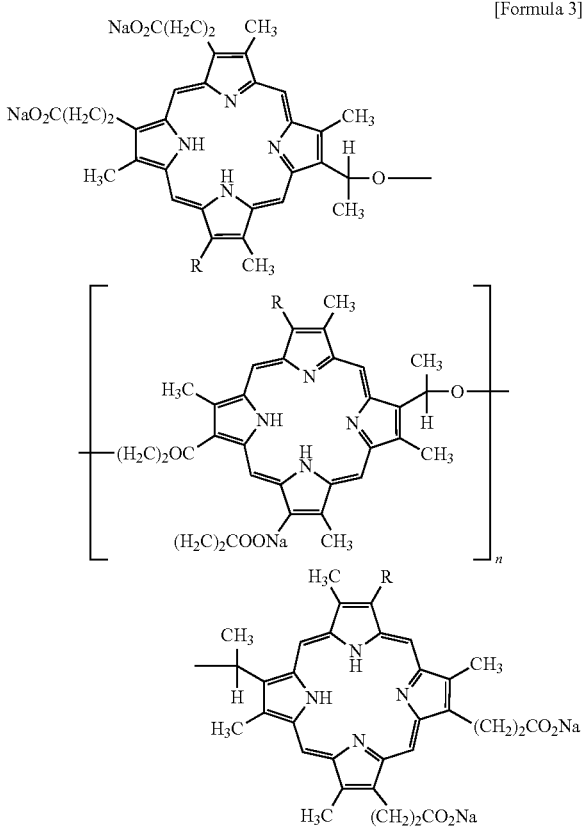

In Formula 3,

R is each independently —CH=CH$_2$ or —CH(OH)—CH$_3$, and n is an integer from 0 to 6.

2. The photosensitizer of claim 1, wherein the conjugate does not exhibit cytotoxicity during blood circulation or in normal tissue, is targeted, accumulated and decomposed selectively in cancer tissue or cancer cells, and produces singlet oxygen or free radicals when near-infrared wavelength light is applied, thereby exhibiting cytotoxicity.

3. The photosensitizer of claim 2, wherein when the conjugate is targeted and accumulated in cancer tissue or cancer cells, the linkage between an ester bond of the hydroxypropyl methylcellulose and the porfimer sodium photosensitizer is cleaved by an enzyme in vivo and fluorescence interference is released to exhibit fluorescence.

4. The photosensitizer of claim 1, wherein the photosensitizer further comprises a target protein, an antigen-presenting cell, a stem cell-derived exosome, and a liposome which is used as a photosensitizer in photodynamic therapy.

5. The photosensitizer of claim 1, wherein the photosensitizer further comprises a virus, immune cell, and a vaccine, which is used as a photodynamic immune anticancer therapeutic agent in photodynamic therapy.

6. The photosensitizer of claim 1, wherein the photosensitizer further comprises an anticancer protein, which is used as a photodynamic immune anticancer therapeutic agent in photodynamic therapy.

7. The photosensitizer of claim 1, wherein the photosensitizer is used in treating lung cancer, gastrointestinal cancer, esophageal cancer, skin cancer, and cervical cancer.

\* \* \* \* \*